US011253548B1

(12) United States Patent
Dregalla et al.

(10) Patent No.: US 11,253,548 B1
(45) Date of Patent: Feb. 22, 2022

(54) METHOD OF PRODUCING THE CONSTITUENTS OF A THERAPEUTIC PRODUCT FROM MAMMALIAN CELLS

(71) Applicant: Napa Medical Research Foundation, Napa, CA (US)

(72) Inventors: Ryan Dregalla, Lyons, CO (US); Marko Bodor, Napa, CA (US); Yvette Uribe, Napa, CA (US)

(73) Assignee: Napa Medical Research Foundation, Napa, CA (US)

( * ) Notice: Subject to any disclaimer, the term of this patent is extended or adjusted under 35 U.S.C. 154(b) by 415 days.

(21) Appl. No.: 16/298,669

(22) Filed: Mar. 11, 2019

(51) Int. Cl.
*A61K 35/19* (2015.01)
*A61K 35/28* (2015.01)
*C12N 5/0735* (2010.01)
*C12N 5/078* (2010.01)
*C12N 5/071* (2010.01)

(52) U.S. Cl.
CPC ............ *A61K 35/19* (2013.01); *A61K 35/28* (2013.01); *C12N 5/0606* (2013.01); *C12N 5/0608* (2013.01); *C12N 5/0644* (2013.01); *C12N 2509/10* (2013.01); *C12N 2527/00* (2013.01)

(58) Field of Classification Search
None
See application file for complete search history.

(56) References Cited

U.S. PATENT DOCUMENTS

| 4,749,522 | A | 6/1988 | Kamarei |
| 5,306,637 | A | 4/1994 | Lin et al. |
| 5,380,826 | A | 1/1995 | Castor et al. |
| 5,922,536 | A | 7/1999 | Nivens |
| 2011/0183403 | A1* | 7/2011 | Dierkes ............... C12N 1/066 435/257.1 |
| 2016/0002598 | A1 | 1/2016 | Centeno et al. |

FOREIGN PATENT DOCUMENTS

WO WO-2013157891 A1 * 10/2013 ............. A61P 17/00

OTHER PUBLICATIONS

Kim et al. (WO 2013/157891 A1) (EPO machine translation) (Year: 2013).*

* cited by examiner

*Primary Examiner* — Emily A Cordas
(74) *Attorney, Agent, or Firm* — Timothy Snyder (57) ABSTRACT

A method of producing the constituents of a therapeutic product from mammalian cells is described herein. Cells are isolated from a mammalian source. The cells are exposed to supercritical carbon dioxide ($SCCO_2$) for 1 to 30 minutes, where the $SCCO_2$ is maintained at a pressure of 1071 pounds per square inch (PSI) and a temperature of 31.1 to 45 degrees Celsius during the exposure. The exposure dissociates the cellular membranes of the cells to release intramembrane components therein to produce constituents of the therapeutic product. The mammalian cells may include at least one of platelets, stem cells, germ cells, and somatic cells. The methods described herein are particularly advantageous for releasing and capturing therapeutic intramembrane components from platelets and alpha-granules.

19 Claims, 6 Drawing Sheets

METHOD OF PRODUCING THE CONSTITUENTS OF A THERAPEUTIC PRODUCT FROM MAMMALIAN CELLS

CROSS-REFERENCE TO RELATED APPLICATIONS

Not Applicable

FEDERALLY SPONSORED RESEARCH OR DEVELOPMENT

Not Applicable

INCORPORATION BY REFERENCE OF MATERIAL SUBMITTED ON A COMPACT DISK

Not Applicable

BACKGROUND OF THE INVENTION

The intramembrane components of certain mammalian cell types and platelets are known to have therapeutic effects for orthopedic, neurologic, spinal, dental, cosmetic, and dermal applications. For example, platelets and platelet lysates have been extensively used to help treat arthritis and aid in wound repair. Platelets, as well as other cell types (e.g., stem cells), contain several therapeutic components such as growth factors, cytokines, and other proteins and molecules that can accelerate the healing process, reduce inflammation and scar tissue formation. As such, various techniques have been developed to release or capture these intramembrane components in a time effective and aseptic manner for therapeutic use. These techniques include, for example, exposure of the cells to one or more freeze-thaw cycles, ultrasonification, exposure of the cells to a hypotonic or lysing solution. Unfortunately, experimental data has consistently shown sub-optimal lysis efficiency (less than 50% as characterized by the number of lysed cells in a given sample), failure to target intra-platelet granules and the degradation or un-folding of native therapeutic proteins. Further, these other methods rely on multiple cycles (freeze/thaw, ultrasonic pulses) to increase lysis over time. Each of these methods takes at least 30 minutes to achieve the desired outcome.

Thus, there exists a need for an improved method to release intramembrane therapeutic components from within a mammalian cell to produce a product for therapeutic use which can be accomplished residue free, without toxins, in less than 30 minutes and with greatly improved concentrations of bioactive therapeutic intramembrane components.

FIELD OF THE INVENTION

The present invention generally relates to the production of therapeutic products from mammalian cells and in particular to a method of producing an enhanced product with the use of super-critical carbon dioxide.

SUMMARY OF THE INVENTION

A method of producing the constituents of a therapeutic product from mammalian cells is described herein. The method generally includes the following: Cells are isolated from a mammalian source. The cells are exposed to super-critical carbon dioxide ($SCCO_2$) for 1 to 30 minutes, where the $SCCO_2$ is maintained at a pressure of 1071 to 5000 pounds per square inch (PSI) and a temperature of 31.1 to 45 degrees Celsius during the exposure. The exposure disassociates the cellular membranes of the cells to release intramembrane components and produce constituents of the therapeutic product. The mammalian cells may include platelets, stem cells, germ cells, and somatic cells.

Following the exposure, the $SCCO_2$ is off-gassed where the $SCCO_2$ is maintained above freezing temperatures, transiting directly to liquid and/or gaseous phase carbon dioxide without the formation of a solid (i.e. dry ice). This serves to protect the intramembrane components from freezing to preserve the integrity, conformation, and bioactivity of the intramembrane components.

With regard to mammalian platelets, they are suspended as a mixture in fluid or concentrated into a pellet where at least 90% of the supernatant is removed then exposed to the SCOO2 under the specific pressure and temperature conditions noted above.

Alpha-granules from the platelets are also exposed to the $SCCO_2$, thereby dissociating the granule membrane to release bioactive intramembrane alpha-granule components. These components may be used in various final therapeutic forms including: (i) directly as is; (ii) mixed with a biological fluid, saline, or water; (iii) or further isolated by centrifuging the mixture to pellet the intramembrane platelet components and intramembrane alpha-granule components and then reconstituted in a biological fluid, saline, or water. The intramembrane platelet components and intramembrane alpha-granule components are advantageously soluble in the final therapeutic product for administration.

The methods described herein result in at least 50% of the platelets releasing their intramembrane platelet components when exposed to $SCCO_2$ in solution, and at least 93% of the platelets releasing their intramembrane components for pelleted platelets within 10 minutes of exposure.

BRIEF DESCRIPTION OF THE DRAWINGS

In the figures, identical structures, elements or parts that appear in more than one figure are generally labeled with the same numeral in all the figures in which they appear. The dimensions of components and features shown in the figures are generally chosen for convenience and clarity of presentation and are not necessarily shown to scale. The figures are listed below.

Figures

FIGS. 5A to 5D depict dot plots of the raw results from the flow cytometry testing, where FIGS. 5A and 5B depict the results of the control group for platelets suspended in a liquid, and FIGS. 5C and 5D depict the results of the SCOO$_2$ treated group for platelets suspended in a liquid.

FIGS. 6A to 6D depict dot plots of the raw results from the flow cytometry testing, where FIGS. 6A and 6B depict the results of the control group for pelleted platelets, and FIGS. 6C and 6D depict the results of the SCOO$_2$ treated group for pelleted platelets.

DETAILED DESCRIPTION OF THE DRAWINGS

The present invention has utility as an improved method to release intramembrane components from within mammalian cells to produce the constituents of a therapeutic product for therapeutic use. Embodiments of the method described herein are particularly advantageous in maximizing the amount of intramembrane components for therapeutic use while maintaining the integrity, conformation, therapeutic efficacy, and bioactivity of the intramembrane components. Therapeutic applications for the final therapeutic product produced by the methods described herein include orthopedic, neurologic, spinal, dermal, dental, and cosmetic applications. The final product may also be used in vitro as a growth supplement to culture media intended for research or ex vivo cell expansion for therapeutic use. The following description of various embodiments of the invention is not intended to limit the invention to those specific embodiments, but rather to enable any person skilled in the art to make and use this invention through exemplary aspects thereof.

It is to be understood that in instances where a range of values are provided that the range is intended to encompass not only the end point values of the range but also intermediate values of the range as explicitly being included within the range and varying by the last significant figure of that range. By way of example, a recited range of 1 to 4 is intended to include 1-2, 1-3, 2-4, 3-4, and 1-4.

As used herein, "mammalian cells" refer to platelets, stem cells, germ cells, and somatic cells from a mammalian source. Mammalian sources illustratively include a human or other primate, canine, feline, sheep, whale, or horse.

Also as used herein, "intramembrane components" refers to components residing within a lipid membrane. The components illustratively include growth factors, angiogenic factors, serotonin, cytokines, growth hormones, growth signals, proteases, protease inhibitors, extracellular matrix constituents, adhesion proteins, and other components contributing to cellular or bodily growth, repair, or maintenance. Exemplary components include matrix metalloproteinase, tissue inhibitors of metalloproteinase, thrombin, thrombospondins, von Willebrand factor, ADP, serotonin transforming growth factors, fibroblast growth factors, platelet-derived growth factors, human growth factors, vascular endothelial growth factors, fibrinogen, fibronectin, interleukins and interleukin receptors, angiogenins/angiopoietins, and insulin-like growth factors and insulin-like growth factor-binding proteins.

Figure 1:
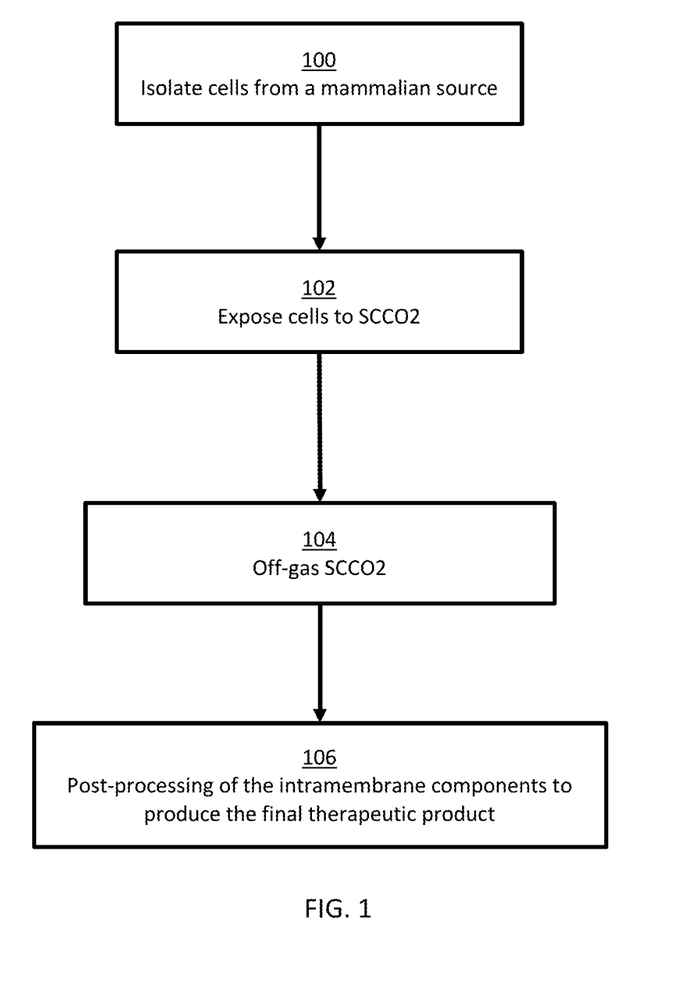
FIG. 1 depicts a flowchart for a method of producing the constituents of a mammalian cell or platelet derived therapeutic product in accordance with the embodiments of the invention.

With reference now to the drawings, FIG. 1 depicts a method to release intramembrane components from a mammalian cell to produce the constituents of a therapeutic product. The method generally includes the following steps. Mammalian cells are isolated from a mammalian source [Block 100]. The mammalian cells are exposed to super critical carbon dioxide (SCCO$_2$) [Block 102]. The exposure causes a gentle disassociation of the cellular membranes to release the intramembrane components to produce the constituents of the therapeutic product. The pressure and temperature are monitored and controllable during the exposure to preserve the integrity of the intramembrane components. After exposure, the SCCO$_2$ is off-gassed under controlled conditions to ensure the components do not freeze [Block 104]. The intramembrane components are post-processed to produce the final therapeutic product [Block 106]. Specific embodiments of the method are further described below.

The mammalian cells may be isolated from a mammalian source using techniques known in the art. In a particular embodiment, whole blood is used as the source. Whole blood may be collected from the mammalian source with an anti-coagulant to prevent cellular aggregation. The whole blood is centrifuged, one or more times, to separate the whole blood into two or more fractions rich with different cell types. The desired cells are isolated, which may undergo additional pre-processing steps as described below, or transferred directly to a sample vessel for SCCO$_2$ exposure. It should be appreciated, that the mammalian cells may be isolated from other tissues illustratively including bone, bone marrow, nerves, arteries, and organ tissue using techniques known in the art. After isolation and/or pre-processing, the cells are exposed to SCCO$_2$.

Figure 2:
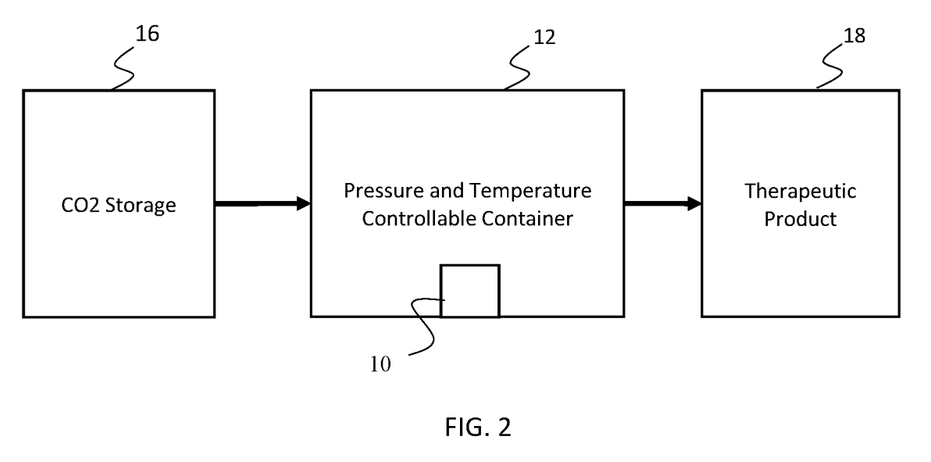
FIG. 2 depicts a diagram for exposing mammalian cells or platelets to supercritical carbon dioxide in accordance with embodiments of the invention.

With reference to FIG. 2, an embodiment of exposing the cells to SCCO$_2$ is shown. A sample vessel 10 having the isolated cells is placed inside a container 12. The container 12 may have temperature and pressure control capabilities to control the pressure and temperature of the carbon dioxide (CO$_2$) inside the container 12. The CO$_2$ may be originally stored in a CO$_2$ tank 16 in a non-super-critical (liquid) state. The non-critical CO$_2$ is then introduced into the container 12, where the CO$_2$ makes direct contact with the cells. As the pressure and/or temperature of the CO$_2$ increases inside the container 12, the CO$_2$ transitions into a SCCO$_2$. The SCCO$_2$ is exposed to the cells for approximately 1 to 30 minutes, and in specific embodiments, no more than 10 minutes. During the exposure, the pressure is maintained between 1071 and 5000 pounds per square inch (PSI) and the temperature is maintained between 31.1 degrees Celsius and 45 degrees Celsius, while in a more preferred embodiment, the pressure is maintained between 1071 PSI and 2000 PSI and the temperature is maintained between 31.1 degrees Celsius and 39 degrees Celsius. During the exposure, the SCCO$_2$ is observed to have a turbulent-appearance, which permeates the cells like a gas and flows like a liquid, inherent of the super-critical nature of CO$_2$.

The exposure to the SCCO$_2$ causes the gentle disassociation of the cellular membranes of the cells to release the intramembrane components. The gentle disassociation of the membrane preserves the integrity, conformation, efficacy, and bioactivity of the intramembrane components, which is further preserved by the limited exposure time to the SCCO$_2$, the controlled pressure, and the controlled temperature. This is in direct contrast to other lysing techniques that utilize longer exposure times, freeze-thaw cycles, and large pressure differentials to 'explode' or stress the cells from their interior (e.g., utilizing osmotic pressure, or suddenly off-gassing to create a stark pressure differential inside the cells via rapid gas gaseous expansion from the liquid CO$_2$ phase), which can greatly reduce the bioactivity, efficacy and conformation of the intramembrane components. Further, these approaches have not been shown to influence intramembrane platelet compartments, such as granules (alpha and dense types), lending little insight as to their therapeutic efficiency. In addition, carbon dioxide is chosen as the medium for membrane disassociation because other supercritical fluids leave a residue and the temperatures required for these other fluids to be in a supercritical phase are well outside physiologic temperatures, which can damage or denature the intramembrane components or be toxic when used therapeutically.

After $SCCO_2$ exposure to the cells, the $SCCO_2$ is off-gassed from the container 12. During off-gassing, the temperature of the intramembrane components are maintained above freezing while slowly releasing the pressure to preserve the native state of the intramembrane components. This slow and temperature controlled off-gassing procedure ensures the cells and intramembrane components are never frozen, which is highly advantageous for producing a superior therapeutic and efficacious product compared to conventional methods.

Once the CO2 is released from the container, the intramembrane components in the vessel 10 are post-processed to produce the final therapeutic product 18. In some embodiments, post-processing includes collecting the intramembrane components after $SCCO_2$ exposure for therapeutic use as is. In other embodiments, therapeutic adjunct are added to the intramembrane components to form the final product. Other post-processing steps may be performed as described below.

Platelet Derived Therapeutic Product

In particular inventive embodiments, the mammalian cells are platelets. Platelets are known to have several intramembrane platelet components for therapeutic use. Obtaining the intramembrane components from the platelets however, is particularly difficult for several reasons. For one, platelets have a larger surface area to volume ratio compared to other cells. In general, as cell volume increases and as the surface-to-volume ratio of the cell diminishes, the more sensitive the cells are to rupture by mechanical disruption; freezing, ultrasonification, etc. Thus, conventional methods to lyse platelets are more extreme and lead to the destruction of therapeutic proteins in the process via unfolding and/or denaturation. Secondly, the platelet cytoskeletal structure is rigid and has a high content of actin and possesses a discoid shape. These features are unique to platelets in both the eukaryotic and prokaryotic world, which make them particularly difficult to rupture. Embodiments of the method described herein have proven to overcome these particular problems.

Platelets may be isolated from a mammalian source using techniques known in the art. If separation is by centrifugation of whole blood, the platelets are isolated accordingly from their corresponding cell fraction. The platelets are typically isolated while suspended in plasma. The platelet and plasma mixture may be transferred to a vessel 10 for direct $SCCO_2$ exposure, or pre-processed further prior to exposure.

In a specific embodiment, the platelets suspended in plasma undergo additional pre-processing steps prior to $SCCO_2$ exposure. In a specific embodiment, pre-processing includes the pelleting of the platelets into a concentrated mass by centrifugation. After centrifugation, greater than 90% of the supernatant is removed above the platelet pellet. The platelet pellet may then be directly exposed to the $SCCO_2$ under the operating conditions as described above. In a particular embodiment, pre-processing may include the removal of the supernatant above the pelleted platelet, where the supernatant is subsequently filtered to remove unwanted proteins, such as fibrin or fibrinogen, or other supernatant components. The pelleted platelets are then re-suspended in the filtered supernatant where the mixture is exposed to $SCCO_2$. In another embodiment, pre-processing includes the re-suspension of the pelleted platelets in another fluid (e.g., water, saline, or other therapeutic compounds), where this mixture is exposed to $SCCO_2$.

The $SCCO_2$ exposure has the same benefits as described above where the platelet membrane is gently disassociated to release the intramembrane platelet components where the integrity, efficacy, and bioactivity of the components are maintained. In addition, $SCCO_2$ exposure maintains the solubility of the components, where the components are soluble in a biological or water based fluid, which is advantageous from a therapeutic administration perspective.

In specific inventive embodiments, the $SCCO_2$ exposure is also capable of disassociating the membrane of alpha-granules. Alpha-granule membranes are likewise difficult to rupture for similar reasons as platelets and any of the conventional methods to do so would affect the integrity and efficacy of the intramembrane alpha-granule components. Alpha-granules contain several therapeutic components not available, or in lower quantity in the cytoplasmic compartment of platelets, including an array of mitogenic proteins, angiogenic proteins, chemokines, anti-inflammatory proteins (including but not limited to CXCL4, thymosin-B4, CXCL7-deriviates, CCL5, IL-10, VEGF, bFGF, PDGF-AB, -BB, AA, EGF, HGF, IGF, TSP-1, vWF, and TGF-beta isoforms). To release these components, the alpha-granules are exposed to the $SCCO_2$ during exposure of the platelets due to the permeability of biological membranes in the presence of SCCO2. In some embodiments, the $SCCO_2$ exposure time is increased for an additional 1 to 10 minutes beyond the exposure time of the platelets. While in other embodiments the platelets and alpha-granules are collectively exposed to $SCCO_2$ for no more than 30 minutes total, and in some embodiments for no more than 10 minutes total. During the exposure, the same aforementioned pressure and temperature operating conditions are maintained. After exposure, the $SCCO_2$ is off-gassed where the temperature of the intramembrane platelet components and intramembrane alpha-granule components remain above freezing. As such, the components are never frozen to preserve the integrity, efficacy, and bioactivity of those components for therapeutic use.

Following exposure and off-gassing, the intramembrane platelet components and intramembrane alpha-granule components are post-processed to form the final product. For $SCCO_2$ exposure of pelleted platelets with greater than 90% of the supernatant removed, the intramembrane components may be post-processed by re-constituting the intramembrane components and any residual components (e.g., membrane lipids) in a fluid medium such as water, saline, a biological fluid (e.g., plasma, filtered plasma) to form the final product. This final product may be ready for therapeutic use directly. One or more therapeutic adjuncts may also be added as a constituent to the final product. In another embodiment, the intramembrane components and any residual components may be post-processed by harvesting these components directly without re-constitution in a fluid medium to form the final product. The consistency of the non-reconstituted product may be gelatinous in nature, which may be beneficial for wound repair applications. In another particular embodiment, the final product may be subjected to filtration through a 0.22 micron filter or centrifugation to remove residual cell debris and/or further purify the soluble intramembrane components.

For SCOO2 exposure of platelets suspended in solution, post processing may include one or more of the following. In a particular embodiment, the intramembrane components, any residual components, and the suspension fluid (e.g., plasma) are directly packaged or used as the final therapeutic product. In another embodiment, the intramembrane components and any residual components are concentrated by centrifugation or evaporation of the suspension fluid where greater than 50% of the suspension fluid is removed from the mixture. This concentrated mixture is then packaged as the final product. In a further embodiment, greater than 90% of the suspension fluid is removed from the intramembrane/residual components by centrifugation or evaporation. Subsequently, the intramembrane/residual components are packaged directly as the final therapeutic product in a gelatinous form, or the intramembrane/residual components are re-suspended in another fluid medium such as water, saline, or a biological fluid. In addition, the final product may be subjected to filtration through a 0.22 micron filter or centrifugation to remove residual cell debris and/or further purify the soluble intramembrane components. It should be appreciated that any of the above products may further include one or more therapeutic adjuncts added thereto.

Example with Experimental Data

The following is an example of producing the constituents of a platelet based therapeutic product by employing one or more embodiments of the methods described herein.

45 milliliters (mL) of whole blood was collected with an anticoagulant solution (Anticoagulant Citrate Dextrose (ACD)) to a final concentration of 20%. The whole blood was centrifuged in series to fractionate the whole blood. Platelet rich plasma (PRP) was collected from the appropriate fraction. 2 mL of PRP was added to 8 different vials. Each vial was centrifuged at 3500 rotations per minute (rpm) for 8 minutes to pellet the platelets. The supernatant (platelet poor plasma) was removed with a pipette. 4 of the vials were re-suspended with 2 mL of saline and 20% ACD for $SCCO_2$ exposure. The 4 other vials were left as platelet pellets for $SCCO_2$ exposure. Table 1 outlines the contents and $SCCO_2$ exposure times for each vial.

TABLE 1

Experimental Conditions

| Vial | Contents | Exposure Time |
|---|---|---|
| Vial 1 | Liquid Phase PRP | 10 minutes |
| Vial 2 | Liquid Phase PRP | 15 minutes |
| Vial 3 | Liquid Phase PRP | Control - no exposure |
| Vial 4 | Liquid Phase PRP | Duplicate Control - no exposure |
| Vial 5 | Pelleted Platelets | 10 minutes |
| Vial 6 | Pelleted Platelets | 15 minutes |
| Vial 7 | Pelleted Platelets | 20 minutes |
| Vial 8 | Pelleted Platelets | Control - no exposure |

For the vials exposed to $SCCO_2$, the temperature and pressure of the $SCCO_2$ was maintained within the ranges as described above. The $SCCO_2$ was likewise off-gassed according to the embodiments described above.

After exposure and off-gassing, each pelleted platelet condition was re-suspended in 2 mL of saline with 20% ACD. Each sample was then stained with a CD61 fluorescent marker (platelet marker) and a CD62P fluorescent marker (alpha-granule marker) (dual signals ($CD61^+$ and $CD62P^+$) indicate an activated platelet) for flow cytometry testing to determine the number of intact platelets and activated platelets. Flow cytometer gates were set on unlabeled controls for platelets, activated platelets, and regions where leukocytes and red blood cells (RBCs) reside (size and granularity).

Figure 3:
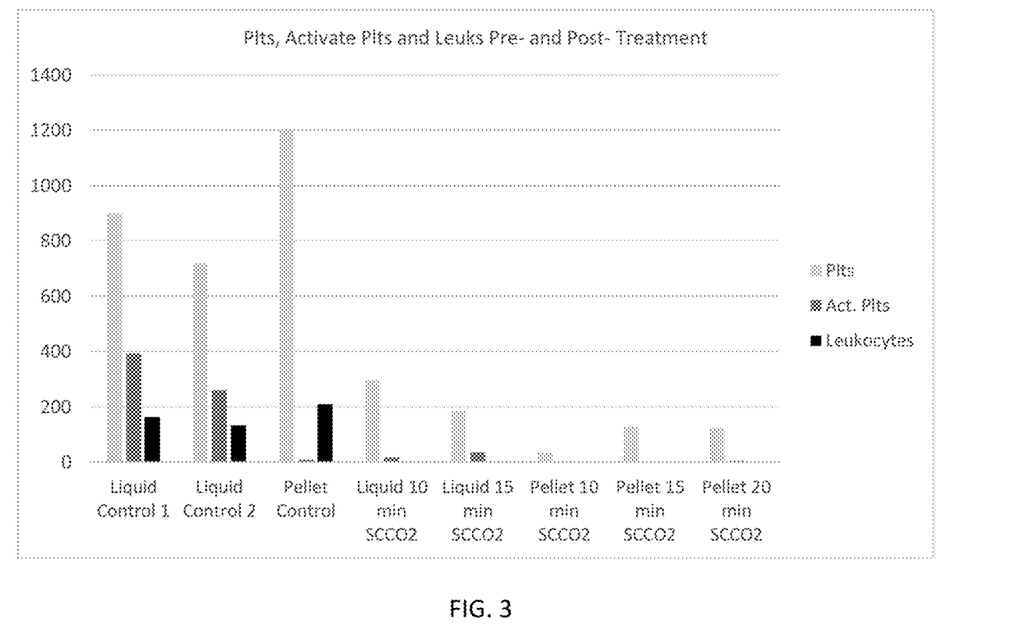
FIG. 3 demonstrates efficiency of lysis of platelets, activated platelets and leukocytes exposed to SCCO2 at 1071 PSI and a temperature of 31.1-45° C. in accordance with the embodiments of the invention. The columns on the left show relative numbers of platelets and cells in control aliquots and aliquots subsequently exposed to $SCCO_2$, while columns on the right indicate relative numbers of platelets and cells remaining after exposure to SCCO2 for 10 and 15 minutes.
Figure 4:
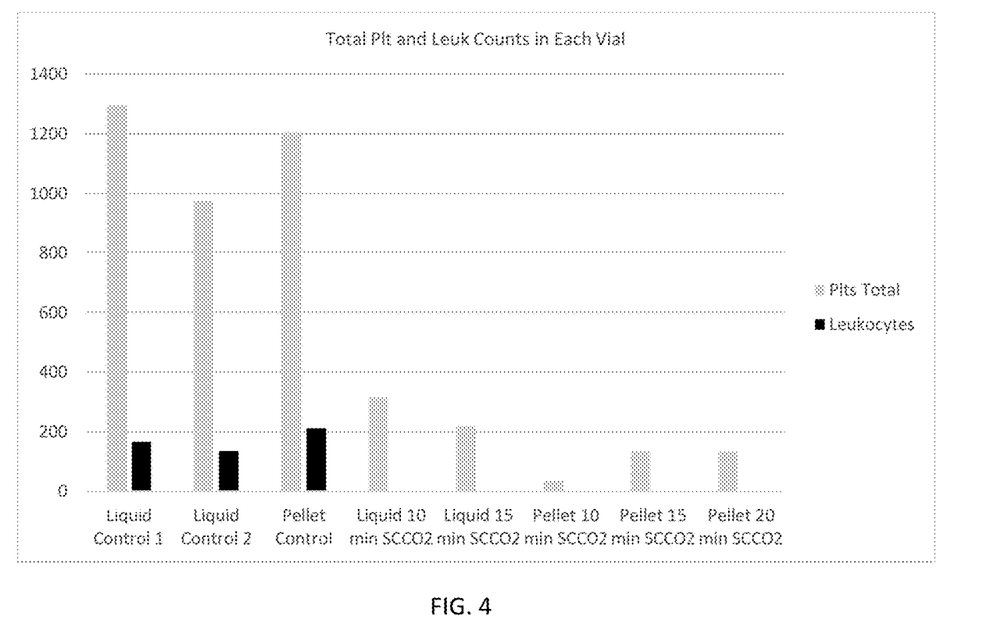
FIG. 4 depicts the results of total platelets and leukocyte control conditions and $SCCO_2$ exposure conditions to determine the number of total intact platelets and intact leukocytes post SCCO$_2$ exposure in accordance with embodiments of the invention.

FIG. 3 depicts the results of the flow cytometry testing for platelets, activated platelets, and leukocytes for the control conditions and the exposed conditions. As shown in FIG. 3, the number of remaining platelets, activated platelets, and leukocytes dramatically decreased due to the $SCCO_2$ exposure for all the exposure conditions. Further, no $CD62P^+/CD61^-$ alpha-granules were detected as further described with reference to FIGS. 5A to 6D, indicating that the platelet membranes disassociated along with these granules (the dissociation of the platelet membranes alone would lead to the detection of the granules in the solution). Exposing the cells for longer than 10 minutes did not appear to greatly affect the disassociation of the cells. FIG. 4 depicts the results for the total platelet count and leukocyte count for the control conditions and exposure conditions. Here, it can be seen that exposure to the pelleted platelets resulted in a greater number of platelets having their membranes disassociated than the exposure to the platelets suspended in a fluid. The actual counts of the cells and percentage of residual platelets and leukocytes are shown in Tables 2 and 3, respectively.

TABLE 2

Average Cell Counts Before and After $SCCO_2$ Exposure

| | Liquid Control | Pellet Control | Liquid SCCO2 | Pellet SCCO2 |
|---|---|---|---|---|
| Platelets | 1135.29 | 1206.21 | 267.57 | 99.95 |
| Leukocytes | 149.41 | 211.12 | 0.8 | 0.6 |

TABLE 3

Percentage of Residual Cells Before and After $SCCO_2$

| | Liquid Control | Pellet Control | Liquid SCCO2 | Pellet SCCO2 |
|---|---|---|---|---|
| Platelets | 1 | 1 | 0.24 | 0.083 |
| Leukocytes | 1 | 1 | 0.0054 | 0.0028 |

Tables 2 and 3 summarize the data presented in FIGS. 3 and 4, representing the average cell counts and percentages of residual cells in the respective controls and after 10-minute and 20-minute SCCO2 exposures. Prior to averaging, there was no significant difference in platelet, leukocyte or alpha granule counts between the 10- and 20-minutes exposure times (shown in FIGS. 3 and 4). Overall, $SCCO_2$ exposure for platelets suspended in a fluid resulted in approximately 75% of platelets having their platelet membranes disassociated, while $SCCO_2$ exposure to pelleted platelets resulted in approximately 93% of platelets having their platelet membranes disassociated. This disassociation efficiency is unprecedented given that other platelet lysis methods for clinical applications are less than 15% per treatment cycle (e.g., freeze-thaw methods).

Figure 5A:
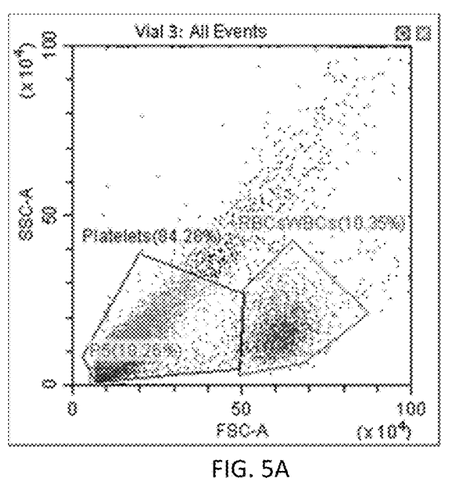
Figure 5B:
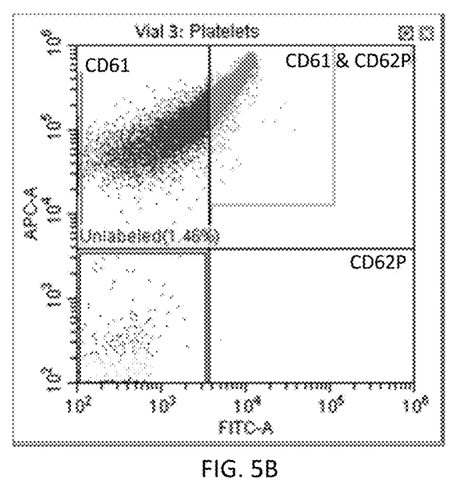
Figure 5C:
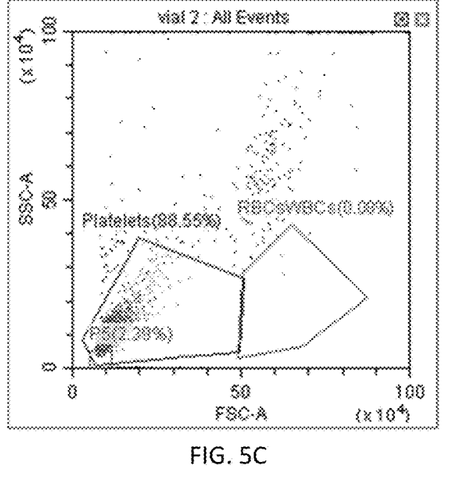
Figure 5D:
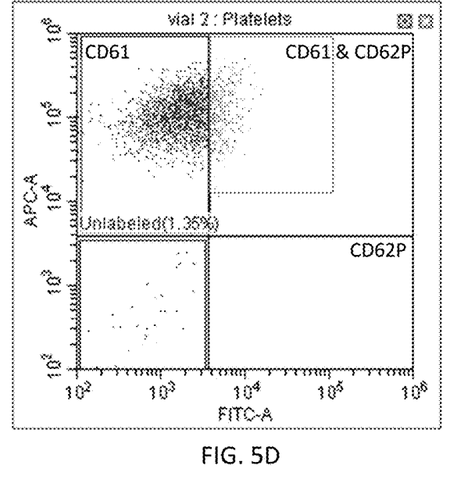

With reference to FIGS. 5A to 6D, dot plots with the results of the flow cytometry testing are shown illustrating the dissociation of the platelet and alpha granule membranes for the liquid phase platelet conditions and the pelleted platelet conditions. FIG. 5A depicts all cellular events for the control group in the liquid phase platelet condition, and FIG. 5B depicts the fluorescent marker results (unlabeled lower left quadrant), CD61+ (upper left quadrant), CD61+ & CD62P+ (upper right quadrant), and CD62P+ (lower right quadrant)) of the gated platelet population in the control group of the liquid phase platelet condition. These are compared with FIGS. 5C and 5D, where FIG. 5C depicts all cellular events for the $SCCO_2$ treated group in the liquid phase platelet condition, and FIG. 5D depicts the fluorescent marker results of the gated platelet population in the treated group. Of particular note is the lack of alpha granules (CD62P+/CD61−) detected in the lower right quadrant of FIG. 5D. Alpha granules would have been in the lower right quadrant after $SCCO_2$ exposure only if the platelet membranes disassociated and not the alpha granules. And because the alpha granules are present inside the platelet membrane, it is to be expected to see no alpha granules in the lower right quadrant of the control group FIG. 5B.

Figure 6A:
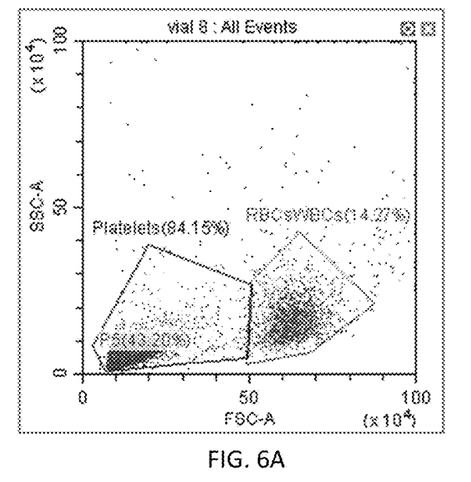
Figure 6B:
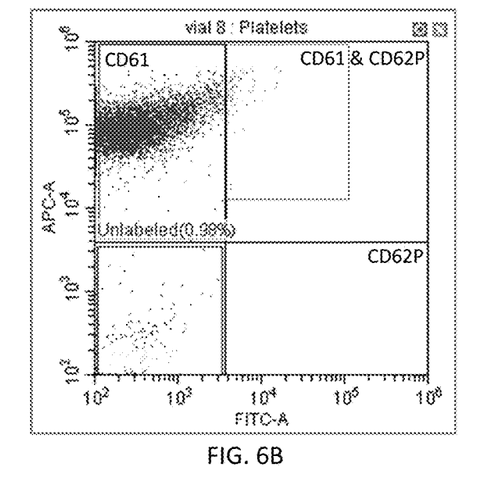
Figure 6C:
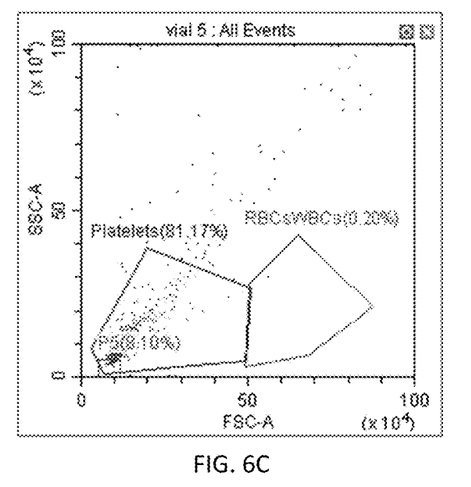
Figure 6D:
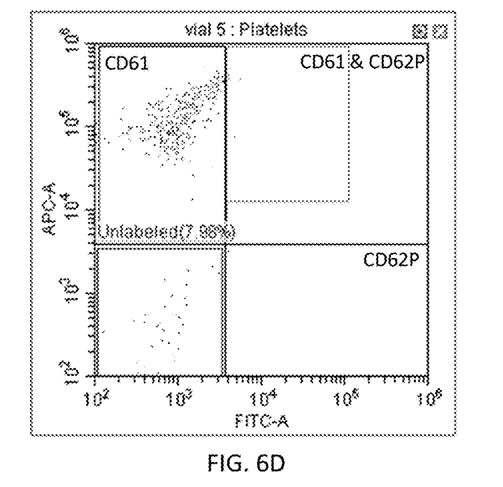

Likewise, FIG. 6A depicts all cellular events for the control group in the pelleted platelet condition, and FIG. 6B depicts the fluorescent marker results of the gated platelet population in the control group of the pelleted platelet condition. These are compared with FIGS. 6C and 6D, where FIG. 6C depicts all cellular events for the $SCCO_2$ treated group in the pelleted platelet condition, and FIG. 6D depicts the fluorescent marker results of the gated platelet population in the $SCCO_2$ treated group. As above, there are no alpha granules (CD62P+/CD61−) detected in the lower right quadrant of FIG. 5D. Alpha granules would have been in the lower right quadrant after $SCCO_2$ exposure if the platelet membranes dissociated but not the alpha granules.

Lastly, it should be appreciated that following $SCCO_2$ exposure the intramembrane components were readily soluble in a biological or water based fluid and available for direct therapeutic use.

OTHER EMBODIMENTS

While at least one exemplary embodiment has been presented in the foregoing detail description, it should be appreciated that a vast number of variations exist. It should also be appreciated that the exemplary embodiment or exemplary embodiments are only examples, and are not intended to limit the scope, applicability, or configuration of the described embodiments in any way. It should be understood that various changes may be made in the function and arrangement of elements without departing from the scope as set forth in the appended claims and the legal equivalents thereof.

What is claimed is:

1. A method of producing the constituents of a therapeutic product from platelets and alpha-granules, comprising:
    isolating platelets from a mammalian source; and
    exposing the platelets and their alpha-granules to supercritical carbon dioxide ($SCCO_2$) to release intramembrane platelet components and intramembrane alpha-granule components to produce constituents of the therapeutic product, wherein the intramembrane alpha-granule constituents are soluble in the final therapeutic product.

2. The method of claim 1, wherein the platelets and alpha-granules are exposed for 1 to 30 minutes.

3. The method of claim 2, wherein the $SCCO_2$ is maintained at 31.1 to 45 degrees Celsius and 1071 to 5000 pounds per square inch (PSI) during the exposure.

4. The method of claim 3, further comprising off-gassing the $SCCO_2$ after an exposure time, wherein the $SCCO_2$ is maintained above freezing temperatures during the off-gassing.

5. The method of claim 3, wherein the platelets and alpha-granules are exposed for no more than 10 minutes and the $SCCO_2$ is maintained at 31.1 to 39 degrees Celsius and 1071 to 1200 PSI during the exposure.

6. The method of claim 1, wherein the isolated platelets are suspended in a fluid to form a mixture thereof, wherein the mixture is exposed to the $SCCO_2$.

7. The method of claim 6, wherein the platelets and alpha-granules are exposed to the $SCCO_2$ for 1 to 30 minutes.

8. The method of claim 7, wherein the $SCCO_2$ is maintained at 31.1 and 45 degrees Celsius and 1071 to 5000 pounds per square inch (PSI) during the exposure.

9. The method of claim 8, further comprising off-gassing the $SCCO_2$ after an exposure time, wherein the $SCCO_2$ is maintained above freezing temperatures during the off-gassing.

10. The method of claim 8, wherein the platelets and alpha-granules are exposed for no more than 10 minutes and the $SCCO_2$ is maintained at 31.1 to 39 degrees Celsius and 1071 to 1200 PSI during the exposure.

11. The method of claim 1, wherein the intramembrane platelet components and intramembrane alpha-granule components in the mixture is either: used directly as the final therapeutic product; mixed with at least one of a biological fluid, saline, or water for use as the final therapeutic product; or isolated by centrifuging the mixture to pellet the intramembrane platelet components and intramembrane alpha-granule components and re-suspended in at least one of a biological fluid, saline, or water for use as the final therapeutic product.

12. The method of claim 1, wherein at least 50% of the platelets release their intramembrane platelet components.

13. The method of claim 1, further comprising pelleting the isolated platelets into a concentrated mass and removing at least 90% of the supernatant, wherein the concentrated mass with the removed supernatant is exposed to the $SCCO_2$.

14. The method of claim 13, wherein the platelets and alpha-granules are exposed for 1 to 30 minutes.

15. The method of claim 14, wherein the $SCCO_2$ is maintained at 31.1 and 45 degrees Celsius and 1071 to 5000 pounds per square inch (PSI) during the exposure.

16. The method of claim 15, further comprising off-gassing the $SCCO_2$ after an exposure time, wherein the $SCCO_2$ is maintained above freezing temperatures during the off-gassing.

17. The method of claim 15, wherein the intramembrane platelet components and intramembrane alpha-granule components are re-suspended in at least one of a biological fluid, saline, or water for use as the final therapeutic product.

18. The method of claim 15, wherein the platelets and alpha-granules are exposed for no more than 10 minutes and the $SCCO_2$ is maintained at 31.1 to 39 degrees Celsius and 1071 to 1200 PSI during the exposure.

19. The method of claim 1, wherein at least 93% of the platelets release their intramembrane platelet components.

* * * * *